United States Patent [19]

Burton et al.

[11] 4,269,827
[45] May 26, 1981

[54] PROCESS AND COMPOSITION FOR REDUCING BLOOD PRESSURE

[75] Inventors: James A. Burton, Amesbury; Edgar Haber, Weston, both of Mass.

[73] Assignee: The Massachusetts General Hospital, Boston, Mass.

[21] Appl. No.: 162,082

[22] Filed: Jun. 23, 1980

[51] Int. Cl.³ .................... A61K 37/00; C07C 103/52
[52] U.S. Cl. ............................. 424/177; 260/112.5 R
[58] Field of Search ................. 424/177; 260/112.5 R

[56] References Cited

PUBLICATIONS

Poulsen, et al., Biochim. et Biophys. Acta., (452), 1976, 533–537.
Poulsen, et al., Chem. Abstr., 79, (1973), 123025a.
Poulsen, et al., Chem. Abstr., 83, (1975), 74424b.

*Primary Examiner*—Delbert R. Phillips
*Attorney, Agent, or Firm*—Paul J. Cook; Marvin C. Guthrie

[57] ABSTRACT

A blood pressure reducing composition which inhibits renin in vivo which composition has the peptide structure Z-His-Pro-Phe-His-X-X-Val-Tyr-Y wherein the xs are the same or different and are phenylalanine, a chlorinated phenylalanine or tyrosine, Y is a charged amino acid and Z is proline or polyproline having up to 5 prolyl residues.

5 Claims, No Drawings

PROCESS AND COMPOSITION FOR REDUCING BLOOD PRESSURE

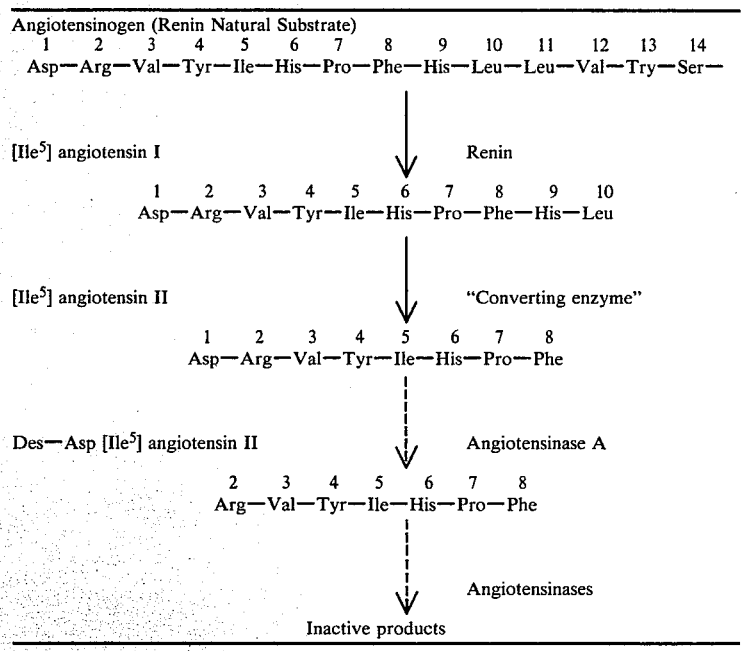

BACKGROUND OF THE INVENTION

The Government has rights in this invention under Grant No. 2 R01 HL 19517-04 granted by the National Institute of Health.

This invention relates to a method and composition for reducing blood pressure.

Renin is a proteolytic enzyme released into the blood in response to a variety of stimuli. Once in the plasma, renin cleaves a specific peptide bond in its natural protein substrate, angiotensinogen, to yield angiotensin I. Renin has no known direct physiologic effect other than to cleave its substrate. Angiotension I has no known biological activity, but is rapidly cleaved by the carboxydipeptidase-converting enzyme (E.C.3.4.15.1), to yield angiotensin II. Angiotensin II has many biological activities including increasing blood pressure both directly by a vascoconstrictor response and indirectly by sodium and fluid retention. Excessive release of renin, in a variety of pathological conditions, can thus result in life-threatening hypertension. Accordingly, there has been a concerted research effort aimed at providing means which inhibit renin and prevent generation of angiotensin I and II, thereby to provide a means for reducing hypertension.

The amino acid sequence of amino terminal 14 residues of equine renal substrate is shown schematically below. Preliminary evidence indicates substantial differences may exist in the amino acid sequence of natural substrate from other species. Renin cleaves this protein substrate between the leucyl residues at position 10 and 11 to release the decapeptide angiotensin I. Angiotensin I is in turn cleaved between residues 8 and 9 by converting enzyme to yield the active hormone, angiotensin II. Aminopeptidases further degrade angiotensin II by removing the amino terminal aspartic acid. The resultant heptapeptide, sometimes called angiotensin III, is believed by some investigators to be the primary mediator of adrenal cortical aldosterone secretion. Angiotensin II and III have very short half-lives in the circulation and are further degraded to smaller inactive peptides.

Prior to the present invention, there has been no known agent which blocks the direct action of renin on its substrate and which also has potential clinical utility. Two types of agents that block steps in the generation of angiotensin have been used in man prior to this invention. They are: converting enzyme inhibitors and angiotensin receptor blockers. Angiotensin converting enzyme blockers such as Teprotide and Captopril which block the conversion of the inactive decapeptide angiotensin I to the active angiotensin II also prevent the degradation of a vasodilating hormone bradykinin. Excessive concentrations of bradykinin are believed to cause undesirable effects including hypotension. Angiotensin receptor site blockers are analogs of angiotensin II and have all been shown at certain dose ranges in all individuals to be partial agonists and cause rises in blood pressure. Two classes of renin inhibitors have been developed and undergone some testing. One class of compounds are analogs of lysolecithin. These materials have low affinity for renin and are unlikely to be useful drugs. The second class of compounds, pepstatins, are bacterial products. They inhibit all acid proteases including enzymes such as pepsin and cathepsin B and are thus non-specific. Pepstatin and semi-synthetic derivatives of these compounds have been tested in experimental animals. Their relatively lower binding affinity for renin than for other enzymes as well as their lack of selectivity make it unlikely that they will be utilized in clinical applications.

The person skilled in this art thus is reluctant to utilize these agents in hypertension. Therefore, it would be desirable to provide a means for inhibiting the action of renin on its natural substrate by competing with the natural substrate for the active binding site or the renin molecule.

As disclosed in the prior art, it has been found that the octapeptide, His-Pro-Phe-His-Leu-Leu-Val-Tyr, is the smallest peptide component of the tetradecapeptide substrate which functions effectively as a substrate for renin. Accordingly, it has been proposed in the prior art to provide modifications of this molecule and other similar fragments from natural substrate which would function as a competing inhibitor for the reaction between renin and its substrate. A wide variety of such substitute compounds have been proposed wherein different amino acids replace component amino acids in the active octapeptide. A large number of such synthetic peptides have been found to be active as inhibitors for renin in vitro. However, prior to this invention, no such synthetic peptide has been found which has both the requisite solubility in the blood stream and bonding to renin to afford its use in the treatment of human hypertension. For example, modification of the octapeptide inhibitor by replacing either leucyl residue with the D-enantiomorph yields inhibitors which are not cleaved by renin. In addition, the [D-leu⁶] octapeptide binds renin one order of magnitude more tightly than the parent octapeptide at pH 5.5. Attempts to inhibit renin with this modified octapeptide at pH 7.5 indicate it to be inactive at this pH. Therefore, this modified octapeptide is useless for in vivo application. In addition, it has been proposed to add one or more proline molecules to the N-terminal histidine of the octapeptide, thereby to improve solubility at physiologic pH. However, while some solubility improvement has been noted, inhibition activity is still too low for the resultant modified peptide to be useful for in vivo application. Replacement of the valyl residue with threonyl at the seven position of the octapeptide provides an octapeptide which is twice as soluble at physiologic pH but is inactive in inhibiting renin. Attempts to increase solubility by modifying the C-terminus carboxyl of the peptide such as by the addition of serinol has not resulted in the expected solubility of the resultant product. Furthermore, various attempts to improve solubility by the addition of charged groups to the N-terminus of various renin inhibitors have not resulted in increased solubility which permits in vivo application of the resultant product for use as a renin inhibitor. Attempts also have been made to increase binding while retaining the desired solubility of peptides by substituting amino acids at the binding site of the active octapeptide. Thus, for the series of octapeptides containing Leu-Tyr, Leu-Phe, Phe-Phe rather than the Leu-Leu at the cleavage site of natural substrate, binding constants of 12, 4, and 1 M, respectively have been obtained. However, none of these compounds has the requisite half-life to afford sufficient utility for in vivo use.

Accordingly, it would be highly desirable to provide a substrate for renin which has a high bindinng activity for renin at physiologic pH. Furthermore, it would be highly desirable to provide such a substrate which is soluble in human plasma and which has a half-life in the circulatory system which is long enough to be useful and which can be subsequently metabolized for excretion.

SUMMARY OF THE INVENTION

The present invention provides peptide compositions which are active in binding renin at physiologic pH and which are soluble in human plasma. In addition, the present invention provides peptide compositions which have a sufficiently long half-life to afford their use in vivo for the purpose of binding significant amounts of renin present in the blood of a patient. The peptides of this invention are prepared by solid phase peptide synthesis wherein protected amino acids are anchored to a polymeric substrate and are sequentially added one on to another until the desired amino acid sequence is attained. Thereafter, the peptide is cleaved from the polymer substrate with concommitant removal of the side chain protecting groups. The resultant polypeptide then is purified by chromatography. The peptides of this invention have been found to be significantly effective in reducing blood pressure in vivo for primates.

DESCRIPTION OF SPECIFIC EMBODIMENTS

The peptides of the present invention are represented by formula I:

Z-His-Pro-Phe-His-X-X-Val-Tyr-Y          Formula I wherein His is histidine, Pro is proline, Phe is phenylalanine, Val is valine and Tyr is tyrosine. The Xs are the same or different and are an aromatic or aliphatic amino acid selected from the group consisting of phenylalanine, a chlorinated phenylalanine such as chlorophenylalanine, dichlorophenylalanine, leucine, isoleucine, valine or the like or tyrosine. Y is a charged amino acid residue at the C-terminus of the polypeptide which can be either positively or negatively charged including lysine, arginine, ornithine or aspartic acid. This charged amino acid residue has the effect of both extending the half-life of the polypeptide molecule in vivo and increasing the solubility thereby to render the polypeptide effective in inhibiting renin in vivo. Z can be either proline or polyproline having up to about 5 prolyl residues in series. The proline or polyproline residue renders the polypeptide molecules specific for primate renin. Particularly useful polypeptides for purposes of the present invention are those wherein Z is proline, Y is lysine and the Xs can be the same or different and can be phenylalanine or monochlorophenylalanine. The polypeptides of this invention are characterized by a solubility in an aqueous medium at physiologic pH of between about 800 and about 3000 μM, an inhibition constant for renin ($K_i$) of between about 0.5 and about 20 μM and a half-life in vitro as measured by rate of loss of radioactively labeled peptide from the circulation of between about 1 and about 15 minutes.

The polypeptides of this invention can be produced by any conventional means for joining amino acid residues to form a polypeptide chain. A particularly desirable procedure involves solid phase peptide synthesis wherein amino acid residues are joined sequentially to a polymer base under reaction conditions to protect the amino acids until the desired peptide sequence is formed. Thereafter, the peptide chain is cleaved from the polymer base and the constituent amino acid side chains are deprotected. This yields the desired peptide sequence which then can be purified such as by chromatography.

A suitable polymer base comprises beads formed from polystyrene wherein a portion of the phenyl groups are substituted with $CH_2Cl$ groups. The first amino acid bonded to the polymer is the amino acid which ultimately becomes the charged residue at the C-terminus of the final peptide chain. Bonding is conveniently effected by reacting the protected amino acid with the chloromethylated polymer under condensation conditions to establish an ester linkage between the C-terminal amino acid and the polymer. Suitable conditions to effect the desired condensation while maintaining protection of the amino group and side chain of the acid are to reflux with triethylanine in alcohol for 24 hours. When the amino acid residue has more than one amino or imino group, the imino or amino group which is to be linked by an amide bond with the next succeeding amino acid residue is protected less strongly than the other amino or imino groups which are to remain protected throughout formation of the desired peptide. After the first amino acid has been bonded to the polymer substrate, the next amino acid is added by the following procedure. Generally, the protected amino acid on the polymer first is deprotected at the amino group to be condensed with the carboxyl group of the next amino acid by an acid solution such as trifluoroacetic acid or methane sulfonic acid. The salt thus formed by deprotection then is neutralized such as with triethylanine or diisopropylethylamine. Condensation with the second amino acid then is effected in the presence of a dehydrating agent, preferably dicyclohexylcarbodiimide, usually at normal room temperature. The polymer then is washed, deprotected, neutralized and reacted with the next amino acid in the desired peptide sequence under the conditions set forth above. The desired peptide product than is obtained by treating the polymer with a strong acid such as hydrofluoric acid, hydrogen bromide/acetic acid or PdOAc/H$_2$ which effects cleavage of the peptide from the polymer while deprotecting any protected side chain groups. A particularly suitable deprotecting agent is hydrogen fluoride containing 1% anisole. The peptide is recovered by extraction into a weak acid such as acetic acid, 0.01 NHCl or the like. This product then can be purified by chromatography.

Particularly suitable peptide products obtained by this invention are:

Pro-His-Pro-Phe-His-Phe-Phe-Val-Tyr-Lys

Pro-His-Pro-Phe-His-Leu-ClPhe-Val-Tyr-Lys

Pro-His-Pro-Phe-His-Leu-Tyr-Val-Tyr-Lys

Pro-His-Pro-Phe-His-Leu-Phe-Val-Tyr-Lys

The compositions of this invention are particularly useful for administration to animals, particularly humans for reducing blood pressure. Compositions of this invention can be administered intravenously. When administered alone, suitable dosages depend upon the inhibitor constant of the particular peptide being administered. The dosage should be sufficient to provide substantial inhibition of renin while at the same time not be so large as to substantially increase the risk of orthostatic hypotension. Generally suitable dosages are between about 0.2 and about 2 mg per kg body weight. The inhibition constant of a composition of this invention is determined by the degree with which the composition inhibits reaction of renin with its substrates. This is determined as follows:

The peptide being tested is dissolved in 0.01 N HCl and the pH adjusted to pH 7.5 to obtain high concentrations of peptide. The peptide solution is diluted further to appropriate concentrations with 0.1 M Tris HCL-albumin.

First, to determine $K_m$ renin (0.006 Goldblatt unit/ml) is incubated for 2 hrs. at 37° with incremental concentrations of Tetradecapeptide substrate varying between 3 and 108 $\mu$M in a volume of 160 $\mu$l at pH 7.5 in 0.1 M Tris HCl containing 0.5% albumin. The release of angiotensin I is determined by radioimmunoassay, Haber et al., *J. Clin. Endocrinol. Metab.* 29, 1349, (1969). To determine the inhibitor constant ($K_i$), a parallel series of experiments are performed exactly as described above but in the presence of a single concentration (1-100 $\mu$M) of the inhibitory peptide which gives 50% inhibition. The cross-reaction of the tetradecapeptide with antibody is about 1% and less than 0.5% with the renin inhibitors both before and after exposure to renin. Controls for cross-reactivity are performed with each experiment and appropriate corrections are made when significant, Poulsen et al., *Scand. J. Clin. Lab. Invest.* 31, *Suppl. No.* 132, 1, (1973).

The inhibitor constant is calculated as previously described, Poulsen et al., *Scand. J. Clin. Lab. Invest.* 31, *Suppl. No.* 132, 1, (1973), from a weighted least-squares fit of a Lineweaver-Burk plot. Each point is given a weight proportional to the initial velocity, Dowd et al, *J. Biol. Chem.* 240, 863, (1965).

To determine $K_m$ in plasma, 20 $\mu$l aliquots of serial dilutions of plasma are incubated with 5 $\mu$l of human renin (4×10$^{-3}$ GU/ml); 5 $\mu$l of a solution containing 3 M Tris HCl (pH 7.3), 200 mM EDTA, 12 mM 2,3-dimercaptopropanol, and 25 mM 8-hydroxyquinoline; and 10 $\mu$l of 0.1 M Tris HCl (pH 7.5) containing 0.5% albumin. The mixture is incubated for 45 min at 37° and then cooled to 0°. Complementary amounts of plasma are then added as 20 $\mu$l of a plasma dilution in 0.1 M Tris HCl (pH 7.5) containing 0.5% albumin to give the same amount of plasma protein in all tubes. Tracer and antibody (1000 $\mu$l) are then added following the radioimmunoassay procedure described by Poulsen et al, *J. Clin. Endocrinol. Metab.* 39, 816, (1974). Data for the standard curve is collected in the same medium kept at 4°. To determine $K_i$ parallel series of experiments are performed in which the 10 $\mu$l Tris buffer is replaced with 10 $\mu$l of a solution containing between 2-100 $\mu$M inhibitor, respectively.

The following examples illustrate the present invention are not intended to limit the same.

EXAMPLE I

This example illustrates the preparation of the decapeptide, Pro-His-Pro-Phe-His-Phe-Phe-Val-Tyr-Lys. The initial solid phase support used in this example was chloromethylated cross-linked polystyrene, 200-400 mesh, 0.74 mequiv of Cl$^-$/g. In the first step, the polymer beads was modified by refluxing 1.54 g of N$\alpha$-t-butyloxycarbonyl, N$\alpha$-2chlorobenzyloxycarbonyl lysine (Boc-Lys (2ClZ)) with 2.5 g of the polymer beads, 25 ml of ethanol and 0.46 ml of triethylamine for 24 hours. Analysis showed 201 micromoles of lysine/g of polymer. This reaction as well as the reactions set forth below with the subsequently employed amino acid residues was conducted in apparatus described previously (Burton et al, *Biochemistry* 14, 1982, (1975). Completeness of amide bond formation reactions was tested with ninhydrin by the method of Kaiser et al, *Anal. Biochem.* 34, 595, (1970). Amino acid analysis was performed on samples of peptidyl-resin dried to constant weight and hydrolyzed for 24 hrs at 110° C. in a mixture of concentrated HCl-acetic acid-phenol (2:1:1) in evacuated tubes.

Subsequent additions of protected amino acid residues to the peptide bound to the polymer were conducted as follows:

30% trifluoroacetic acid in dichloromethane is added to the polymer beads having the C-terminal amino acid bound thereto. The trifluoroacetic acid cleaves the protecting group from the α-amino group of the peptidyl polymer. The trifluoroacetic acid solution is added in two separate aliquots; first for 1 min and then after removal for 30 min. The excess reagent then is removed by suction and the polymer beads washed 4 times with dichloromethane. Thereafter, the peptidyl polymer beads are neutralized with 10% triethylamine in dichloromethane in 2 aliquots for 1 min and for 15 min. Then the beads are washed 4 times with dichloromethane. A five-fold excess of the next amino acid to be added to the peptide chain is added as a 0.25 M solution to the beads with stirring. Subsequently, a five-fold excess of dicyclohexylcarbodiimide as a 1.0 M solution in dichloromethane is added to activate the carboxyl group of the amino acid residue to be added and thereby effect reaction with the amino terminus of the peptide chain bound to the polymer beads. During this reaction, stirring is effected for 50 min. Thereafter, extra dichloromethane is added and stirring is effected for an additional 60 min. Excess solution then is removed from the beads by filtration and the beads then are washed 6 times each for 1 min, twice with ethanol, then dichloromethane, then ethanol, and then twice more with dichloromethane.

Following this reaction procedure, the amino acid residues were added to the polymer substrate in the following sequence: tyrosine protected with 2-bromobenzyloxycarbonyl; valine; phenylalanine; phenylalanine; histidine protected with tosyl; phenylalanine; proline; histidine protected with tosyl and proline. The α-amino groups of each amino acid is protected with t-butyloxycarbonyl (Boc) group.

The protected decapeptide is then cleaved from the polymer with hydrogen fluoride-anisole (9:1) with stirring at 0° C. for 1 hr. After evaporation of the HF and anisole at high vacuum, the peptide is separated from the polymer beads by extraction and filtration. The residue was extracted 3 times with aliquots of 10% acetic acid solution and the combined extracts were filtered, lyophilized and transferred to a tarred vial with additional acetic acid solution and relyophilized to yield 262 mol of crude decapeptide (53%).

The crude decapeptide (345 mg) was dissolved in 17 ml of 25% acetic acid, the solution filtered, and the clear filtrate chromatographed on Sephadex G-25 (2.5×118 cm), eluted with 25% AcOH solution (V/V) at a flow rate of 90 ml/hur. Fractions eluting between 440 ml and 510 ml were pooled and lyophilized. The resultant decapeptide composition (211 mg) was redissolved in 10 ml of 0.01 N HCl, the solution filtered, and the firtrate then chromatographed on Bio-Gel p-2 (2.5×116 cm), eluted with 0.01 N HCl at a flow rate of 85 ml/hr. Fractions eluting between 555 ml and 705 ml were pooled and lyophilized. The fraction was homogeneous and contained 148 μM peptide (30%): acid hydrolysis of a small sample showed ratios of Pro, 1.74 mol; His, 1.88 mol; Phe, 2.91 mol; Val, 0.92 mol; Tyr, 0.94 mol; Lys, 0.94 mol.

High performance liquid chromatography of this fraction on a $C_{18}\mu$ Bondapak column eluted with a 1% $H_3PO_4$ 15% acetonitrile using a gradient to 39% acetonitrile showed a single symmetrical peak eluting at 37% acetonitrile as measured by v-v absorbance at 280 nM. The sample gives a single ninhydrin positive spot after thin layer chromatography in 3 systems on silica gel (205μ). $R_f(T3)$; $R_f(T4)$; $R_f(T6)$. T3: 1-Butanol-Pyridine-acetic acid-water (75:50:15:60). T4: 1-Butanol-Pyridine-acetic acid-water (143:42:14). T6: t-propanol-conc. ammonium hydroxide (140:66). On high voltage electrophoresis in pH 3.5 (0.1 M) sodium acetate-acetic acid, the peptide migrates toward the cathode as a single spot which is readily detectable with ninhydrin. The molar extinction coefficient at 280 nM is 443 (0.15 M saline). The sample is pyrogen free.

The inhibitory effect of the decapeptide in human plasma was determined as follows: human blood was drawn in ice cold tubes containing EDTA as anticoagulent and the plasma was immediately separated at 4° C. The plasma was from a normal person receiving an estrogen containing medication for birth control which insured a high renin substrate concentration. Substrate concentration was determined by measuring angiotensin I concentration by radioimmunoassay after incubation of plasma diluted 1:10 in the phosphate albumin buffer (pH 7.4) with 10 μl of human renin solution (0.006 GU/ml) for 1, 2, 3 and 4 hrs in order to convert renin substrate completely to angiotensin I. EDTA, BAL (2,3-dimercapto-1-propanol) and 8-hydroxyquinoline were added as angiotensinase inhibitors, Haber et al, *J. Clin. Endocrinol.* 29, 1349, (1969).

The determination of the inhibitory constant was performed in the manner set forth above except that a plasma serially diluted in phosphate buffer (pH 7.4) replaced the tetradecapeptide. The same angiotensinase inhibitors were added.

Determination of Inhibitor Constant

The tetradecapeptide is a renin substrate releasing angiotensin I after cleavage between leucyl residues at positions 10 and 11.

A mixture of inhibitory decapeptide and substrate tetradecapeptide was expected to compete for the catalytic site of renin. Specific antibody is used to measure angiotensin I release from the decapeptide. Since the antibody does not cross-react significantly with either the decapeptide or its cleavage products, angiotensin I may be measured directly in the reaction mixture.

The cross-reactivity of the tetra decapeptide was measured after incubation of the above-mentioned concentrations without renin for 1 hr at 37° and then added to the radioimmunoassay mixture. The apparent angiotensin I values obtained were expressed in percentage of the molar decapeptide concentration added and was 1%.

The cross-reactivity of the decapeptide and its cleavage products was determined by incubation with renin but without tetra decapeptide at the relevant concentration for 1 hr at 37°.

The cross-reactivity was expressed as for the decapeptide and never exceeded 0.5%. The determination for $K_i$ was followed by this series of cross-reactivity experiments and the generated angiotensin I concentrations were subtracted from the small apparent angiotensin I values caused by decapeptide as well as inhibitor peptides and their cleavage products.

The decapeptide should act as a competitive inhibitor for the reaction between renin and tetradecapeptide substrate. The rate of cleavage between renin and decapeptide will therefore be given by Dixon and Webb, Enzymes, New York, N.Y., Academic (1964), $$v = \frac{V}{1 + \frac{K_m}{S}(1 + \frac{I}{K_i})}$$

V and $K_m$ being maximal velocity and Michaelis constant, respectively, for the reaction between renin and tetradecapeptide. The concentration of the decapeptide is called I. The $K_i$ is the inhibitor constant.

In Vitro Inhibition of Renin

In vitro inhibition of human renin was performed at pH 7.4 as described (Burton, J. et al., *Biochemistry* 14, 3892–3898, 1975) to demonstrate that the inhibitory constant ($K_i$) of the peptide is 2 μM.

In Vitro Inhibition of Plasma Renin Activity

The peptide in saline (1 mM) was added to pooled human plasma having a plasma renin activity of 2Z ng $ML^{-1}$ $hr^{-1}$. Measurement showed the inhibition of plasma renin activity was proportional to the concentration of added inhibitor with 50% inhibition occurring at 45 μM (59 mg/L).

In Vivo Inhibition of Plasma Renin Activity

The decapeptide was tested in vivo in Macaque monkeys weighing approximately 5 kg in which the right kidneys were removed surgically and which were on a salt-free diet. The test monkeys were induced to produce renin by an operation in which an inflatable cuff was placed about the abdominal aorta which was connected to a tube extending through the skin of the monkey which in turn was connected to a hand-held pump. When it was desired to induce the production of renin in the monkey, the cuff was inflated restricting blood flow to the remaining kidney. Within 15 min, mean arterial blood pressure of the sodium-depleted monkey had risen about 30 Torr (mm Hg). Injection of the peptide inhibitor in saline at a dose of 2 mg/kg caused a decrease in blood pressure to prior normotensive levels (105 Torr). Smaller doses of the peptide decreased blood pressure proportionally to the amount of peptide given.

Infusions of the peptide in saline (0.2 mg/kg-1 min) will block the use in blood pressure caused by administration of sufficient human renin to raise mean arterial pressure 20 Torr without affecting a similar use in pressure caused by administration of either angiotensin I or angiotensin II.

In a normal monkey, not deprived of sodium, the peptide has no significant effect on blood pressure.

We claim:

1. A blood pressure reducing composition which inhibits renin in vivo having the peptide structure:

Z-His-Pro-Phe-His-X-X-Val-Tyr-Y wherein the Xs are the same or different and are selected from the group consisting of phenylalanyl, tyrosyl and a chlorinated phenylalanyl, Y is a charged amino acid residue selected from the group consisting of lysyl, arginyl, aspartyl and glutamyl and Z is selected from the group consisting of prolyl and polyprolyl having up to 5 prolyl residues.

2. The compound of claim 1 wherein the Xs are phenylananyl, Z is prolyl and Y is lysyl.

3. The process for reducing blood pressure in an animal afflicted with high blood pressure which comprises administering the composition of claim 1 in an amount effective to reduce blood pressure elevations related to renin excess.

4. The process for reducing blood pressure in an animal afflicted with high blood pressure which comprises administering the composition of claim 2 in an amount effective to reduce blood pressure to normal values.

5. The process of claims 3 or 4 wherein the animal is a human.